(12) United States Patent
Gu et al.

(10) Patent No.: US 7,608,588 B2
(45) Date of Patent: Oct. 27, 2009

(54) MINERAL COLLAGEN CHELATES AND METHODS OF MAKING AND USING SAME

(76) Inventors: Jennifer L. Gu, 3622 Cornwall Ct., Rowland Heights, CA (US) 91748; Edward Lee, 3622 Cornwall Ct., Rowland Heights, CA (US) 91748

( * ) Notice: Subject to any disclaimer, the term of this patent is extended or adjusted under 35 U.S.C. 154(b) by 0 days.

(21) Appl. No.: 12/271,293

(22) Filed: Nov. 14, 2008

(65) Prior Publication Data
US 2009/0062181 A1 Mar. 5, 2009

Related U.S. Application Data

(63) Continuation of application No. 11/549,391, filed on Oct. 13, 2006, now Pat. No. 7,495,076.

(60) Provisional application No. 60/596,695, filed on Oct. 13, 2005.

(51) Int. Cl.
*A61K 38/00* (2006.01)
(52) U.S. Cl. .................................... 514/12
(58) Field of Classification Search ............. 514/12
See application file for complete search history.

(56) References Cited

U.S. PATENT DOCUMENTS

| 3,873,296 | A | 3/1975 | Ashmead et al. |
|---|---|---|---|
| 3,969,540 | A | 7/1976 | Jensen |
| 4,020,158 | A | 4/1977 | Ashmead et al. |
| 4,167,564 | A | 9/1979 | Jensen |
| 4,172,072 | A | 10/1979 | Ashmead |
| 4,216,143 | A | 8/1980 | Ashmead |
| 4,216,144 | A | 8/1980 | Ashmead |
| 4,804,745 | A | 2/1989 | Koepff et al. |
| 4,863,898 | A | 9/1989 | Ashmead et al. |
| 6,025,327 | A | 2/2000 | Alkayali |
| 6,716,814 | B2 | 4/2004 | Ericson et al. |
| 6,838,440 | B2 | 1/2005 | Stiles |
| 2003/0087830 | A1 | 5/2003 | Dupont et al. |
| 2004/0053884 | A1 | 3/2004 | Nakagiri et al. |
| 2004/0147445 | A1 | 7/2004 | Levin |

OTHER PUBLICATIONS

Hashida et al., Macromol. Biosci., 2003, 3(1o), 596-603.*
Wedekind et al.; "Methodology for Assessing Zinc Bioavailabiity: Efficacy Estimates for Zinc-Methionine, Zinc Sulfate, and Zinc Oxide;" J. Anim. Sci. 1992, 70:178-187.
Brown et al.; "Laboratory Evaluations of Solubility and Structural Integrity of Complexed and Chelated Trace Mineral Supplements;" 1994 J. Diary Sci 77:181-189.
Jiang et al.; Phosphopeptides Derived from Hen Egg Yolk Phosvitin: Effect of Molecular Size on the Calicium-binding Properties; 2001, Biosci. Biotechnol. Biochem, BC Continued—65(5): 1187-1190.
International Search Report and Written Opinion dated Jan. 22, 2008 in International Application No. PCT/US06/40298.
International Preliminary Report on Patentability for corresponding PCT application PCT/US2006/040298, Mar. 24, 2009, PCT/IB/373/ISA/237.

* cited by examiner

*Primary Examiner*—Maryam Monshipouri
(74) *Attorney, Agent, or Firm*—Timothy X. Gibson, Esq.; Gibson & Dernier LLP

(57) ABSTRACT

Collagen peptide chelated mineral products, pharmaceutical formulations thereof and methods for preparing same are provided. Also provided is a method for generating the optimal size of collagen peptide for optimum mineral chelation as well as optimum biological function for supporting bone health and joint health. Also disclosed are methods of increasing bone density/preventing osteoporosis, of reducing joint pain and/or joint deterioration from osteoarthritis, degenerative joint disease, joint defect, and rheumatoid arthritis.

2 Claims, 1 Drawing Sheet

MINERAL COLLAGEN CHELATES AND METHODS OF MAKING AND USING SAME

CROSS REFERENCE TO RELATED APPLICATIONS

This application is a continuation of U.S. patent application Ser. No. 11/549,391 filed Oct. 13, 2006 now U.S. Pat. No. 7,495,076 and claims the benefit of U.S. provisional Patent Application Ser. No. 60/596,695 filed Oct. 13, 2005, the entireties of which are incorporated herein by reference.

FIELD OF THE INVENTION

The present invention relates generally to dietary supplements, in particular to mineral collagen chelate compounds, compositions containing such compounds, methods for making such compounds and methods of administering same.

BACKGROUND OF THE INVENTION

Collagen has been available in the United States since about 1986 as a food supplement. Collagen I/III can be extracted from calf skin and hydrolyzed for use in nutritional products. U.S. Pat. No. 4,804,745 (Koepff et al.) discloses agents containing collagen peptides produced by enzymatic hydrolysis for the treatment of degenerative joint diseases. These peptides can be obtained from animal skin, animal bones and other connective tissue with average molecular weights of 30-45 kilo-Daltons. U.S. Pat. No. 6,025,327 (Alkayali) and U.S. Pat. No. 6,838,440 (Stiles) disclose therapeutic compositions and method for the protection, treatment and repair of joint cartilage in mammals, comprising hydrolyzed collagen type II between 15 KD to 50 KD average molecular weight obtained from chicken sternal cartilage. In addition, collagen preparations from other animals, such as from donkey skin as in the Chinese traditional Medicine "e-jiao", has also been used for hundreds of years as a skin health/beauty product.

Minerals perform many different functions in the body such as the formation of bone and cartilage, maintenance of fluid and acid/base balance, transportation of oxygen in the blood, normal functioning of muscles and nerves, and production of hormones. Minerals work with vitamins, enzymes, and other minerals in the body to produce their effects. Minerals can be grouped into macro and micro categories. Macro-minerals are needed in greater amounts in the diet, and are found in larger amounts in the body than micro-minerals. Macro-minerals include Calcium (Ca), Phosphorus (P), Magnesium (Mg), Potassium (K), Sodium (Na) and Chloride (Cl), while micro-minerals include Copper (Cu), Iodine (I), Iron (Fe), Manganese (Mn), Selenium (Se), Silicon, and Zinc (Zn). Minerals such as calcium and magnesium are essential for bone and joint health. Minerals such as zinc are necessary for skin health. Iron and copper are important elements for the function of hemoglobin.

The proper balance of minerals in the mammalian body is extremely important and related to the amount of each mineral in the diet, the ability of the animal to absorb the minerals from the intestine, and any disease conditions which could cause excess loss or retaining of various minerals. A high quality mineral supplement which contains the proper balance of minerals can be highly beneficial. However, if supplementation is attempted with minerals of unknown or unreliable bioavailability, it can create imbalances and possibly disrupt nutritional health. Too much or too little of one mineral can affect the action of others. Therefore, it is vital that if supplementation is being practiced that it be carried out using supplements the bioavailability of which are highly predictable and consistent.

It has been shown that minerals can interact with food to form precipitates, thus preventing the mineral from being absorbed properly in the small intestine. Soy protein mineral chelate and rice protein mineral chelate products have been available as more bioavailable organic mineral supplements. Mineral proteinate protects the mineral from unwanted chemical reactions in the gastrointestinal tract, delivering more mineral for optimum absorption in small intestine. Wedekind et al., J. Anim. Sci. 70:178 (1992). According to the Association of American Feed Control Officials (AAFCO) definition, mineral proteinate is the product resulting from the chelation of a soluble salt with amino acids and/or partially hydrolyzed protein. However, some scientific reports that addressed the bioavailability of mineral proteinate supported that mineral proteinate products were superior to mineral supplementation alone, while some indicated that no advantage was provided. Brown T. F. and Zeringue L. K. 1994 J Dairy Sci. 77:181-189.

SUMMARY OF THE INVENTION

A need exists for collagen mineral chelates which have maximum and consistent bioavailability.

While not being bound to any single theory, the inventors believe at least one reason for the disparity in the tested bioavailability of mineral proteinate is the fact that the tested products, which have similar names (e.g. "metal proteinate") are actually produced by different processes that can result in variable concentrations of minerals and variable sizes of peptides between products. The present inventors have found that surprisingly, collagen fragments can be sized to provide optimum bioavailability of minerals in collagen mineral chelate compositions.

In at least one aspect, the present invention relates to preparation of collagen fragments of optimum size for binding minerals in mineral collagen peptide chelated products that can be delivered into organisms for different nutritional and medical purposes. More specifically, this invention relates to compositions including selected mineral cations bound with optimally-sized collagen or hydrolyzed collagen ligands. Depending on the minerals incorporated, these products support bone/joint health, skin/beauty health in animals and humans.

Mineral collagen peptide chelate compounds in accordance with the present invention are useful in producing dietary supplements for supporting joint and bone health. Compositions containing the compounds increase bioavailability of the minerals and stimulate cartilage cell secretion to support healthy bone and joint, and also support skin health/beauty.

Mineral collagen peptide chelate compounds in accordance with the present invention can be included in foods and beverages, food additives, animal feeds and feed additives as well as compositions including pharmaceutically acceptable carriers.

It is therefore an object of the present invention to prepare the mineral proteinates by ensuring that the peptide ligands that bind to the mineral have the optimum size for binding the mineral in addition to maximizing its bioavailability.

Collagen from any source can be used as starting material to produce collagen peptides of optimum size with different minerals for joint/bone health (such as $Ca^{++}$, $Mg^{++}$, $Cu^{++}$, etc) and skin health/beauty (such as Iron, $Cu^{++}$, $Zn^{++}$, $Mg^{++}$, etc).

DETAILED DESCRIPTION OF THE INVENTION

Figure 1:
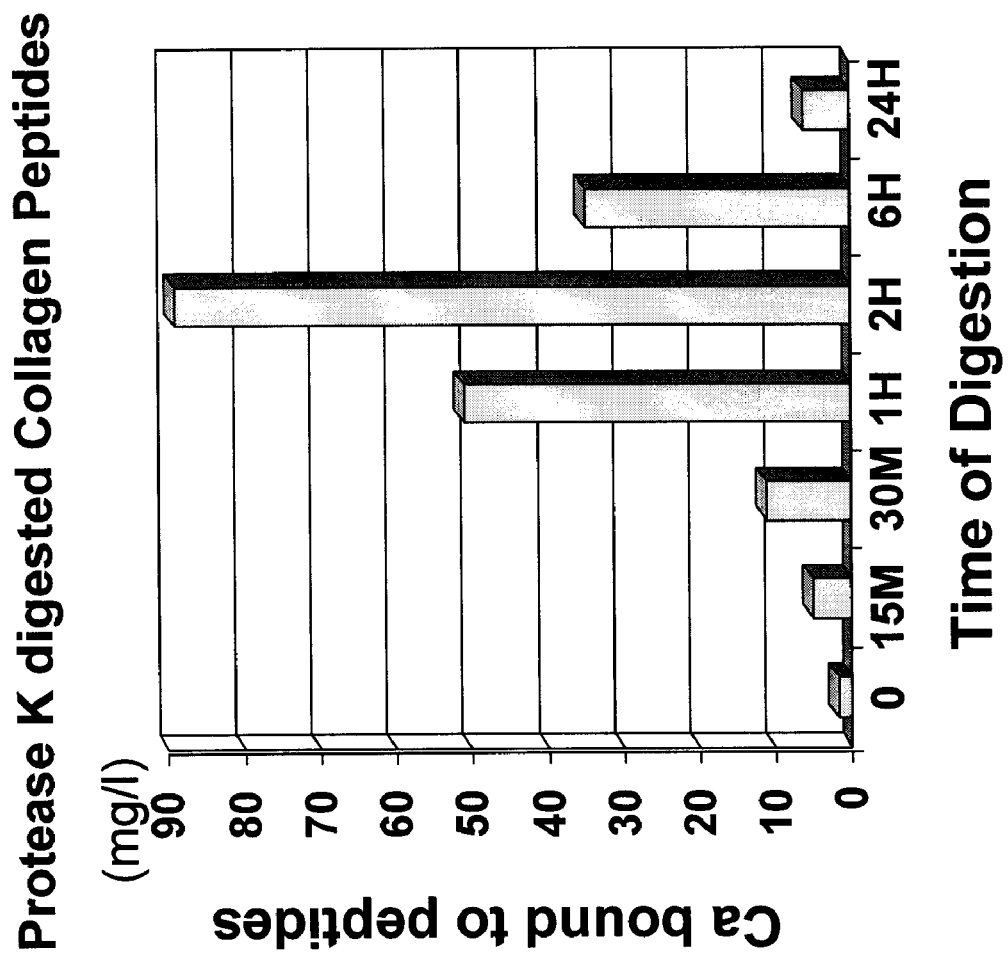
FIG. 1 is a graphical representation of Protease K-digested collagen peptides according to the present invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

Collagen fragments of optimum size are provided for binding minerals in mineral collagen chelates that can be delivered into organisms for different nutritional and medical purposes. As used herein "mineral collagen chelate" describes an association of a metal ion having a valence of two or more to form a structure wherein the positive electrical charges of the metal ion are neutralized by the electrons available through collagen/hydrolyzed collagen. The binding represents physical associations including ionic, covalent, coordinate covalent bonding, or a combination thereof. These compositions are absorbed as a complex or digested into small collagen peptides and minerals released at the site of absorption into biological tissues and, because of either the specific collagen selected or the specific bound metals, migrate to specific tissue target sites where the complex is utilized as is or is dissociated into mineral cations and digested collagens or peptides.

Collagen fragments in accordance with the present invention may be prepared by hydrolyzation. Hydrolyzation of protein is the process of breaking down the ester bond (—O—C=O) or amine (—N—C=O) bond by reaction with H2O. Hydrolyzation can be used to break down protein to smaller peptides through acid (such as HCl), alkaline (such as NaOH) and enzymatic hydrolysis.

Enzymes useful in embodiments employing enzyme hydrolyzation preferably include but are not limited to single enzymes or mixture of enzymes that can digest collagens and other components in tissue, such as, but not limited to collagenase, papain, pepsin, Bromelain, trypsin, bacterial protease, fungal protease, pancreatin and the like.

Any available collagen can be used in the present invention. Animal sources of tissue include but are not limited to chicken, porcine, bovine, fish and the like.

Minerals include one or more members selected from the group including, but not limited to calcium, magnesium, boron, zinc, copper, manganese, iron, silica, and sulfur.

Collagen fragments in accordance with the present invention surprisingly exhibit enhanced mineral binding which increases bioavailability of the minerals.

Collagen fragments prepared in accordance with the present invention are employed to form chelates with any mineral to produce mineral collagen chelate compounds with enhanced bioavailability. When administered, the compounds stimulate cartilage cell secretion to support bone, joint and skin health, depending on the mineral incorporated in the compound.

In one embodiment compositions including mineral collagen chelate compounds are provided in the form of dietary supplements for supporting joint and bone health as well as skin health. Mineral collagen chelate compounds in accordance with the present invention can be included in foods and beverages, food additives, animal feeds and feed additives as well as compositions including pharmaceutically acceptable carriers.

In one embodiment methods for preparing mineral collagen chelate compounds are provided in which collagen fragments of a selected size are combined with a selected mineral to form a mineral collagen chelate. In one embodiment collagen is hydrolyzed, such as by digestion with a selected enzyme for a selected time period, to generate collagen fragments of a desired size and combined with a mineral. In one embodiment collagen source materials such as skin, cartilage from animals and the like are digested using enzymes to collagen peptides with average molecular weight ranging from 0.2 KD to 50 KD, preferably 0.5 KD-2 KD, most preferably about 1-2 KD. To the digested mixture, soluble mineral sources are added and the pH adjusted to form a precipitate.

In another embodiment a method is disclosed of determining the optimum collagen fragment length for binding to a particular mineral. The optimum length is determined by the amount or percentage of mineral that can be bound to the collagen fragment.

EXPERIMENTS

Experiment 1

Bovine hydrolyzed Collagen I/III powder with an average molecular weight of about 4 KD (obtained from AIDP, Inc. of City of Industry, Calif.), was made into a 500 mg/l solution in water and subjected to enzymatic treatment with Collagenase (catalogue # c5138 from Sigma, St. Louis, USA) at 1 mg/ml final concentration at 25° C. water bath with occasional mixing for various amounts of time to render different sized fragments as follows:

Sample 1: Collagen I/III untreated

Sample 2: Collagen I/III Collagenase digestion for 15 minutes

Sample 3: Collagen I/III Collagenase digestion for 30 minutes

Sample 4: Collagen I/III Collagenase digestion for 60 minutes

Sample 5: Collagen I/III Collagenase digestion for 2 hours

Sample 6: Collagen I/III Collagenase digestion for 24 hours

At the end of the treatment, samples were boiled for 5 minutes to stop the enzyme action and cooled to 22° C. in water bath. 100 ml of the digested samples were added to a beaker, mixed constantly with 5 mM $CaCl_2$ (final concentration) for 5 minutes, to which was then added 20 mM (final concentration) sodium phosphate buffer (ph 7.8) and stirred at room temperature for 30 minutes. pH was maintained at 7.8 by adjusting with NaOH as well as HCl, using a pH meter during the stirring process. At the end of 30 minutes, insoluble calcium phosphate precipitates were removed by filtering through a 0.45 uM membrane and the calcium content in the soluble mineral collagen chelate were analyzed using ICP method.

Results were as follows:

| Sample # | Soluble Ca (Calcium bound to collagen) (mg/l) |
|---|---|
| Sample 1 | 1.74 |
| Sample 2: | 29.87 |
| Sample 3: | 72.56 |
| Sample 4: | 3.54 |
| Sample 5: | 5.26 |
| Sample 6: | 4.51 |

It is clear that binding of calcium to collagen depends on the size of collagen fragment, and the maximum amount of binding achieved at 30 minutes of digestion time with Collagenase, which is about 42 times better than the commercially available collagen I/III untreated.

Since hydrolyzed collagen concentration was at 500 mg/l and maximum binding was achieved at 72.56 mg/l, the maximum calcium binding by digested collagen was 72.56 mg/500 mg=14.5% in this experiment.

Experiment 2

The same procedures as experiment 1 were followed except that the enzyme Collagenase was replaced with Protease K from Sigma (Catalogue # p2308) at 100 ug/ml final concentration. Samples were treated at 25° C. as follows:

Sample 1: Collagen I/III untreated

Sample 2: Collagen I/III protease K digestion for 15 minutes

Sample 3: Collagen I/III protease K digestion for 30 minutes

Sample 4: Collagen I/III protease K digestion for 60 minutes

Sample 5: Collagen I/III protease K digestion for 2 hours

Sample 6: Collagen I/III protease K digestion for 6 hours

Sample 7: Collagen I/III protease K digestion for 24 hours

Calcium binding assay were carried out as in experiment 1. Results were as follows:

| Sample # | Soluble Ca (Calcium bound to peptides) (mg/l) |
| --- | --- |
| Sample 1 | 1.74 |
| Sample 2. | 5.045 |
| Sample 3. | 11.19 |
| Sample 4: | 50.96 |
| Sample 5: | 89.07 |
| Sample 6: | 34.94 |
| Sample 7: | 6.284 |

Based on the results and as further shown in FIG. 1, maximum binding of calcium occurred at about 2 hours of Protease K digestion, which resulted in calcium binding of 89.07 mg/l. Since the collagen concentration was 500 mg/l, the maximum calcium binding to collagen was 89.07 mg/500 mg=17.8% calcium binding in this experiment.

To examine the size of the peptide digested with the optimum condition, a MS-HPLC assay for Sample 5 was performed, showing an estimated average molecular weight of 1.629 KD.

Collagen that is prepared in accordance with the present invention releases more epitopes for further mineral binding, and is clearly vastly superior to commercially available collagen in binding minerals. In the case of Experiment 1, about 42 fold more calcium is bound with optimum-size collagen fragments than untreated collagen. In the case of Experiment 2, 51 fold more calcium is bound with optimum-size collagen fragments.

As will be apparent to one having ordinary skill in the art, these experimental conditions can be modified to produce mineral collagen chelate compounds in accordance with the present invention in commercial production quantities, by working out the optimum digestion condition for generating collagen fragments with size ranges preferentially 0.5 KD-2 KD, more specifically about 1-2 KD.

EXAMPLES

Prophetic Example 1

Commercially available collagen I/III from bovine skin is placed in a large tank with water and protease enzymes including, but not limited to Pancreatin, Bromelain, papain, or a mixture of these enzymes under stirring conditions. The digestion conditions are monitored to produce the collagen hydrolysate to average molecular weight between 1-2 KD with MS-HPLC and/or appropriately-sized filters selected to separate collagen fragments of a desired size. The enzymes are inactivated and the solution is filtered. To the filtered solution, a soluble mineral source such as calcium carbonate is added, the mixture is stirred for several hours, and pH is adjusted to 8.5 with NaOH to form a precipitate. The mixture, sprayed dry in a powdered form, contains about 15% of Calcium with average molecular weight 1-2 KD.

Prophetic Example 2

The procedure of example 1 is followed except that fresh skin from bovine, pig or other animals is used instead of the commercially available collagen I/III. The skin is defatted, cut into small pieces and washed prior to addition to the mixing tank.

Prophetic Example 3

The procedure of example 1 is followed except that gelatin, which consists primarily of collagen I/III, is used instead of collagen I/III.

Prophetic Example 4

The procedure of example 1 is followed except that cartilage from bovine, chicken, shark or other animals is used after defatting, cutting into small pieces and washing. These tissues contain mainly collagen II.

Prophetic Example 5

The procedure of example 1 is followed except that more than one soluble mineral source is used. In this Example calcium chloride/magnesium chloride in a 2:1 ratio mixture is employed.

Prophetic Example 6

The procedure of example 1 is followed except that soluble mineral source is ferrous sulfate.

Prophetic Example 7

The procedure of example 1 is followed except that soluble mineral source is zinc chloride.

Prophetic Example 8

The procedure of example 1 is followed except that soluble mineral source is cupric chloride.

Prophetic Example 9

The procedure of example 1 is followed except that soluble mineral source is manganese chloride.

Examples of Supplements

In addition, compounds made in accordance with any of examples 1-9 hereinabove can be formulated with one or more of an amino sugar or a salt thereof, a glycosaminoglycan or a salt thereof, an anti-inflammatory agent such as nonsteroidal anti-inflammatory drugs (NSAIDs) and herb extracts including but not limited to Boswellia, Ashwagandha, Ginger, and Turmeric, and anti-oxidants such as but not limited to Vitamin C and Vitamin E. These formulations can be used in producing dietary supplements, foods and drinks, food additives, animal feeds and feed additives, and drugs which are be administered to individuals/animals to reduce/prevent joint pain or joint deterioration from osteoarthritis, degenerative joint disease, joint defect, and rheumatoid arthritis.

Compounds made in accordance with any of examples 1-9 hereinabove can be formulated with one or more of vitamin D, vitamin C, vitamin K1, and vitamin K2. These formulations can be used in producing dietary supplements, foods and drinks, food additives, animal feeds and feed additives, and drugs which are be administered to individuals/animals to support bone health and reduce or prevent osteoporosis. A preferred composition in accordance with this embodiment includes calcium/magnesium collagen chelate.

Compounds made in accordance with any of examples 1-9 hereinabove can be formulated with one or more of a long chain polysaccharide, such as HA; an anti-oxidant such as Vitamin C, Vitamin E, OPC/grape seed, mangosteen extract, and green tea extract; and nutrients from the following niacin, thiamin, folic acid, iodine, vitamin A, vitamin $B_6$, vitamin $B_{12}$, vitamin D, aloe and mixtures thereof. These formulations can be used in producing dietary supplements, foods and drinks, food additives, animal feeds and feed additives, and drugs which are be administered to individuals/animals to support skin health. A preferred composition in accordance with this embodiment includes ferrous/Zinc collagen chelate.

General Administration and Nutritional/Pharmaceutical Compositions

When used as nutraceutical/pharmaceuticals, the compounds of the invention are typically administered in the form of a nutraceutical/pharmaceutical composition. Such compositions can be prepared using procedures well known in the nutraceutical/pharmaceutical art and comprise at least one compound of the invention. The compounds of the invention may also be administered alone or in combination with adjuvants that enhance stability of the compounds of the invention, facilitate administration of nutraceutical/pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other nutraceutically/pharmacologically active substances. In general, the compounds of this invention are administered in a therapeutically or nutraceutically/pharmaceutically effective amount, but may be administered in lower amounts for diagnostic or other purposes.

Administration of the compounds of the invention, in pure form or in an appropriate nutraceutical/pharmaceutical composition, can be carried out using any of the accepted modes of administration of nutraceutical/pharmaceutical compositions. Thus, administration can be, for example, orally, in the form of solid, semi-solid, lyophilized powder, or liquid dosage forms, such as, for example, tablets, pills, soft elastic and hard gelatin capsules, powders, solutions, suspensions, or the like, preferably in unit dosage forms suitable for simple administration of precise dosages. The nutraceutical/pharmaceutical compositions will generally include a conventional nutraceutical/pharmaceutical carrier or excipient and a compound of the invention as the/an active agent, and, in addition, may include other nutraceutical agents, medicinal agents, pharmaceutical agents, carriers, adjuvants, diluents, vehicles, or combinations thereof. Such nutraceutically/pharmaceutically acceptable excipients, carriers, or additives as well as methods of making nutraceutical/pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients,* A. H. Kibbe (ed.), American Pharmaceutical Ass'n, 2000; and H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular nutraceutical/pharmaceutical formulation will be selected that possess suitable physical characteristics (e.g., water solubility) that is required for the formulation to be efficacious.

Solid dosage forms for oral administration of the compounds include capsules, tablets, pills, powders, and granules. For such oral administration, a nutraceutically/pharmaceutically acceptable composition containing a compound(s) of the invention is formed by the incorporation of any of the normally employed excipients, such as, for example, nutraceutical/pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid nutraceutical/pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing nutraceutical/pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

In all of the above nutraceutical/pharmaceutical compositions, the compounds of the invention are formulated with an acceptable carrier or excipient. The carriers or excipients used must, of course, be acceptable in the sense of being compatible with the other ingredients of the composition and must not be deleterious to the recipient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Nutraceutical/Pharmaceutically acceptable carriers and excipients encompass all the foregoing additives and the like.

Examples of Nutraceutical Formulations

JOINT HEALTH SUPPORT FORMULA
Dosage Recommended: 2 capsules 3 times daily
Serving Size: 1 capsule, 600 mg

| Amount Per Serving: | | % DV |
|---|---|---|
| Calcium Collagen Chelate | 300 | mg |
| Glucosamine HCL | 200 | mg |
| Turmeric extract | 30 | mg |
| Boswellia Serrata Extract (gum) | 25 | mg |
| Ester C comparable formula | 20 | mg |
| Vitamin E | 5 | iu |
| Zinc (picolinate) | 5 | mg |
| Magnesium (carbonate) | 10 | mg |
| Manganese (sulfate) | 1 | mg |
| L-Cystine | 5 | mg |
| L-Lysine | 5 | mg |

BONE HEALTH SUPPORT FORMULA
Dosage Recommended: 2 capsules 3 times daily
Serving Size: 1 capsule

| Amount Per Serving: | | % DV |
|---|---|---|
| Calcium Collagen Chelate | 300 | mg |
| Vitamin D | 120 | IU |
| Vitamin K1 | 25 | ug |
| Vitamin K2 | 25 | ug |
| Ester C comparable formula | 20 | mg |
| Zinc (picolinate) | 5 | mg |
| Magnesium (carbonate) | 10 | mg |
| Manganese (sulfate) | 1 | mg |

Examples of Formulations

A. TABLETS

| Component | Amount per tablet (mg) |
|---|---|
| active substance | 400 |
| lactose | 40 |
| corn starch | 40 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 300 |
| lactose | 20 |
| corn starch | 20 |
| polyvinylpyrrolidone | 15 |
| magnesium stearate | 2 |
| microcrystalline cellulose | 23 |
| sodium-carboxymethyl starch | 20 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 65 |
| Lactose | 10 |
| corn starch | 11.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 460 |
| corn starch | 38.5 |
| magnesium stearate | 1.5 |
| TOTAL | 500 |

The substance and corn starch are mixed and moistened with water. The moist mass is screened and dried. The dry granules are screened and mixed with magnesium stearate. The finished mixture is packed into size 1 hard gelatin capsules.

While the preferred embodiments have been described and illustrated it will be understood that changes in details and obvious undisclosed variations might be made without departing from the spirit and principle of the invention and therefore the scope of the invention is not to be construed as limited to the preferred embodiment.

What is claimed is:

1. A method of supporting mineral homeostasis, promoting bone strength or treatment of diseases associated with a loss of minerals comprising administering to a mammal a composition for oral administration comprising a mineral collagen chelate compound comprising collagen peptides having an average molecular weight of 0.2 KD to 50 KD, at least one mineral and a pharmaceutically acceptable excipient.

2. A method of supporting bone health, increasing bone mineral density and/or increasing bone strength comprising administering to a mammal in need thereof a composition for oral administration comprising a mineral collagen chelate compound comprising collagen peptides having an average molecular weight of 0.2 KD to 50 KD, at least one mineral and a pharmaceutically acceptable excipient.

* * * * *